United States Patent [19]
Yuk et al.

[11] Patent Number: 5,726,212
[45] Date of Patent: Mar. 10, 1998

[54] POLYMER MEMBRANE HAVING A HIGH PERMEABILITY FOR ALKANOL

[75] Inventors: Soonhong Yuk; Sunhang Cho; Haibang Lee, all of Daejun-si, Rep. of Korea

[73] Assignee: Korea Research Institute of Chemical Technology, Rep. of Korea

[21] Appl. No.: 596,364

[22] PCT Filed: Sep. 16, 1994

[86] PCT No.: PCT/KR94/00124

§ 371 Date: Mar. 5, 1996

§ 102(e) Date: Mar. 5, 1996

[87] PCT Pub. No.: WO95/09195

PCT Pub. Date: Apr. 6, 1995

[30] Foreign Application Priority Data

Sep. 27, 1993 [KR] Rep. of Korea .................... 93-19898

[51] Int. Cl.$^6$ .................... C08J 9/26; C08J 9/28; B01D 39/00
[52] U.S. Cl. .................... 521/62; 210/500.29; 210/500.35; 210/500.42; 521/63; 521/64
[58] Field of Search .................... 521/62, 64, 63; 210/500.29, 500.35, 500.42

[56] References Cited

U.S. PATENT DOCUMENTS

| | | | |
|---|---|---|---|
| 4,220,543 | 9/1980 | Yamashita | 521/63 |
| 4,379,454 | 4/1983 | Campbell . | |
| 4,681,584 | 7/1987 | Gale . | |
| 4,698,062 | 10/1987 | Gale . | |
| 4,810,384 | 3/1989 | Fabre | 521/62 |
| 4,968,733 | 11/1990 | Müller et al. | 521/90 |
| 5,158,636 | 10/1992 | Groitzsch . | |

FOREIGN PATENT DOCUMENTS

| | | |
|---|---|---|
| 51-140959 | 12/1976 | Japan . |
| 6291543 | 10/1985 | Japan . |

OTHER PUBLICATIONS

E.M. Renkin; Filtration, Diffusion, and Molecular Sieving Through Porous Cellulose Membranes; J. Gen Physiol. 38; (received for publication May 4, 1954) pp. 225–243.

C.K. Colton, et al; Permeability Studies with Cellulosic Membranes; J. Biomed. Mater. Res. vol. 5 (1971); pp. 459–488.

J. Folkman, et al; The Use of Silicone Rubber as a Carrier for Prolonged Drug Therapy; J. Sug. Res. vol. IV, No. 3 Mar. 1964; pp. 139–142.

S.H. Yuk, et al; One-way Membrane for Transdermal Drug Delivery Systems. I. Membrane Preparation and Characterization; International Journal of Pharmaceutics, 77 (1991); pp. 221–229.

S.H. Yuk, et al; One-way Membrane for Transdermal Drug Delivery Systems. II. Optimization; International Journal of Pharmaceutics 77, (1991) pp. 231–237.

G.M. Zentner, et al; Progestin Permeation Through Polymer Membranes IV: Mechanism of Steroid Permeation and Functional Group Contributions to Diffusion Through Hydrogel Films; Journal of Pharmaceutical Sciences, vol. 68, No. 8 Aug. 1979; pp. 970–975.

*Primary Examiner*—Morton Foelak
*Attorney, Agent, or Firm*—Londa and Traub LLP

[57] ABSTRACT

An alkanol permeation polymer membrane prepared by dissolving biocompatible, non-allergenic polymer capable of being dissolved in polar organic solvent in methylene chloride to prepare a first solution, dissolving cellulose or glycol type polyol compounds in cosolvent composed of alkanol and methylene chloride to prepare a second solution, and mixing the first solution with the second solution, casting the mixed solution on a glass plate with a controlled thickness and evaporating may control the release of drugs effectively.

4 Claims, 2 Drawing Sheets

# POLYMER MEMBRANE HAVING A HIGH PERMEABILITY FOR ALKANOL

BACKGROUND OF THE INVENTION

1. Field of the Invention

The present invention relates to a polymer membrane having a high permeability for alkanol, and more particularly to a alkanol permeation polymer membrane used as a barrier membrane controlling the release rate of drugs and permeation enhancers to assist the delivery of drugs across the skin.

2. Description of Related Art

Transdermal drug delivery system is the drug delivery system that delivers drugs and enhancers across the skin into the body at the constant rate. The transdermal drug delivery system has been proven successful for a number of drug such as nitroglycerin to treat angina or congestive heart failure, scopolamine to treat motion sickness, clonidine to reduce blood pressure, nicotine to treat the prohibition phenomenon, or steroid hormones such as estradiol, testosterone, and progesterone.

General structure of the transdermal drug delivery system includes a reservoir for drugs and permeation enhancers, and a control membrane provided at releasing side for controlling the release of the drug and the permeation enhancers.

In the development of the transdermal drug delivery system such as above, the preparation of the control membrane for controlling the permeation rate of drugs and permeation enhancers is very important.

As a control membrane described above, various alkanol permeation polymer membranes such as MPS, porous PVC sheet, Millepore filter, Celgard porous polypropylene, Ultramicroporous cellulose triacetate (J. Gen. Physiol. 38:225, 1954; J. Biomed. Mater. Res., 5:459, 1971), silicon rubber (J. Sug. Res., 4:139, 1964; I. J. Pharm., 77:221–229, 231–237, 1991), ethylene vinylacetate (EVA) copolymer (U.S. Pat. No. 4,379,454, U.S. Pat. No. 4,681,584 and U.S. Pat. No. 4,698,062) have been reported. However, the conventional alkanol permeation membranes described above are not practically used because the amount of the alkanol permeation enhancer across the alkanol membrane is not enough to enhance the permeation of drugs.

SUMMARY OF THE INVENTION

It is an object of the present invention to provide a novel alkanol permeation polymer membrane which enables a high ethanol permeation to enhance the transdermal delivery of hormone drugs such as estradiol progesterone, and testosterone.

The present invention provides a process for preparing alkanol permeation polymer membrane comprising the steps of: dissolving biocompatible, non-allergenic polymer capable of being dissolved in polar organic solvent in methylene chloride to prepare a first solution; dissolving cellulose or glycol type polyol compounds in cosolvent composed of alkanol and methylene chloride to prepare a second solution; mixing the first solution with the second solution; and casting the mixed solution on glass with the thickness controlled by the use of a film casting knife (Gardner film knife) and evaporating solvent to obtain a membrane.

The biocompatible, non-allergenic polymer capable of being dissolved in polar organic solvent of the present invention is preferably selected from the group consisting of ethylene/vinylacetate copolymer, ethylene/vinylalcohol copolymer, ethylene/ethylacrylate copolymer, vinylidenechloride/vinylacetate copolymer, polymethacrylate, vinyledenchloride and ethylene/vinyloxyethanol copolymer.

The cellulose or glycol type polyol compound of the present invention is preferably one or the mixture selected from the group consisting of hydroxypropylcellulose, hydroxypropylmethylcellulose, polyethyleneglycol, glycerin and ethyleneglycol.

The added amount of said cellulose or glycol type polyol compound is preferably 1 to 30 wt % with respect to said biocompatible, non-allergenic polymer capable of being dissolved in polar organic solvent. If the added amount is beyond the above, then the polymer membrane is not formed and cracked.

The alkanol of cosolvent for cellulose or glycol type polyol compound in the present invention is preferably selected from the group consisting of $C_2$ to $C_8$ alkanols including ethanol, propanol, butanol, pentanol, hexanol, heptanol and octanol.

In the present invention, homogenizer, sonicator or high speed shaker can be used to mix the first solution with the second solution.

The alkanol permeation polymer membrane according to the present invention dose not show the allergy or toxic effect when applying to the skin because the membrane is composed of biocompatible, non-allergenic polymer compound.

The drug of the present invention is preferably selected from the group consisting of nitroglycerin, scopolamine, clonidine, estradiol, testosterone and progesterone.

DETAILED DESCRIPTION OF THE PREFERRED EMBODIMENTS

The following specific examples are illustrative of the present invention, but are not to be considered limiting thereof in any way.

EXAMPLE 1

10 parts of ethylene/vinylacetate (6:4) copolymer was dissolved in 90 parts of methylene chloride, and 10 parts of the solution prepared by dissolving 2 parts of hydroxypropylmethylcellulose in the cosolvent of 48 parts of ethanol and 50 parts of methylenechloride was added. The solution was uniformly mixed and the mixed solution was cast on a glass plate using Gardner film knife and the solvent was evaporated in dry oven of 30° C. to prepare a polymer membrane with the thickness of 70 μm.

EXAMPLE 2

A polymer membrane was prepared according to the procedure of EXAMPLE 1 except that the 1 part of hydroxypropylmethylcellulose was dissolved in the cosolvent. The performance will be substantially the same as for that of EXAMPLE 1.

COMPARATIVE EXAMPLE 1

A polymer membrane was prepared according to the procedure of EXAMPLE 1 except that the hydroxypropylmethylcellulose was not added. The performance will be substantially the same as for that of EXAMPLE 1.

Figure 1:
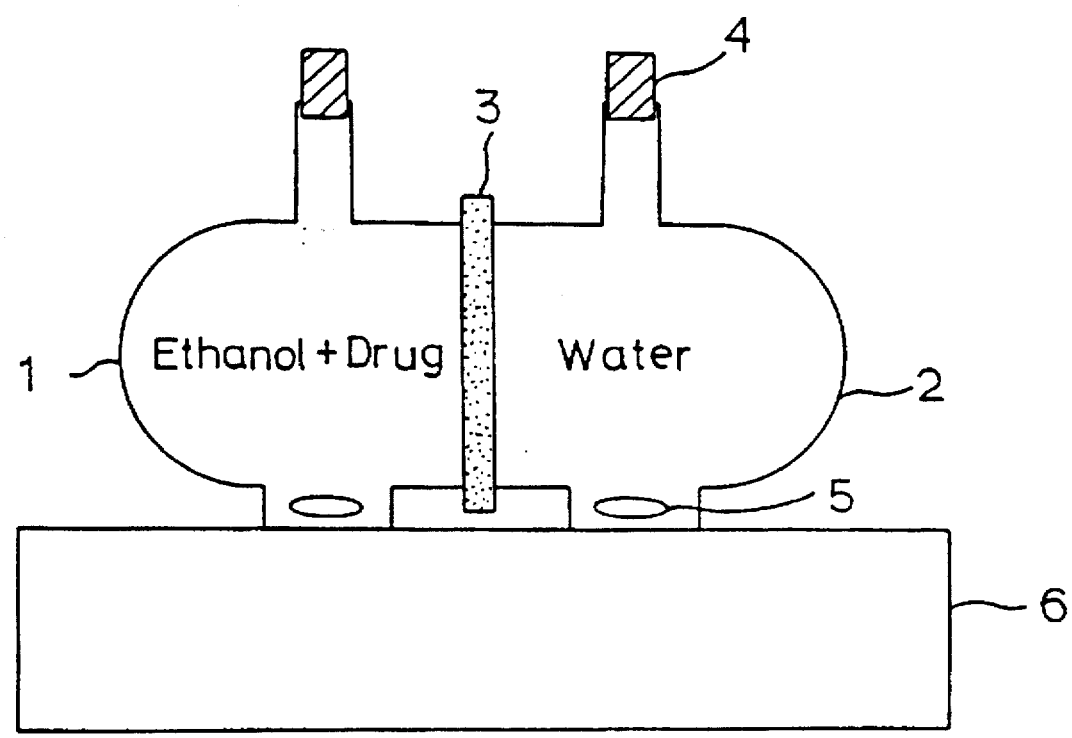
FIG. 1 is a schematic diagram of two compartment permeation cell to observe the amounts of estradiol permeation across through the polymer membrane of the present invention.

Silicon adhesive was cast on polymer membranes prepared by EXAMPLES 1 and 2 and COMPARATIVE EXAMPLE 1 with the thickness of 50 μm and they were cut into disc and diameter is 3 cm. The estradiol permeation rates across the polymer membranes were observed using two compartment glass diffusion cell as shown in FIG. 1. The volume of each compartment was 8.0 ml and area for diffusion was 1.77 $cm^2$. Compartment 1 is filled with 1.2 mg of estradiol in 8 ml ethanol compartment 2 is filled with water. The diffusion cell comprises compartment 1, compartment 2, a membrane 3, a lid 4, a magnetic stirring bar 4 and a magnetic stirrer 5.

TABLE I

| | Permeation Rate of Estradiol across Polymer Membranes (μg/$cm^2$) | | | | | | |
|---|---|---|---|---|---|---|---|
| | 2 | 4 | 6 | 8 | 10 | 20 | 24 |
| EXAMPLE 1 | 0.25 | 0.55 | 0.87 | 1.15 | 1.30 | 1.84 | 2.16 |
| EXAMPLE 2 | 0.15 | 0.39 | 0.56 | 0.79 | 0.94 | 1.43 | 1.61 |
| COMPARATIVE EXAMPLE 1 | 0 | 0 | 0 | 0 | 0.02 | 0.14 | 0.05 |

Figure 2:
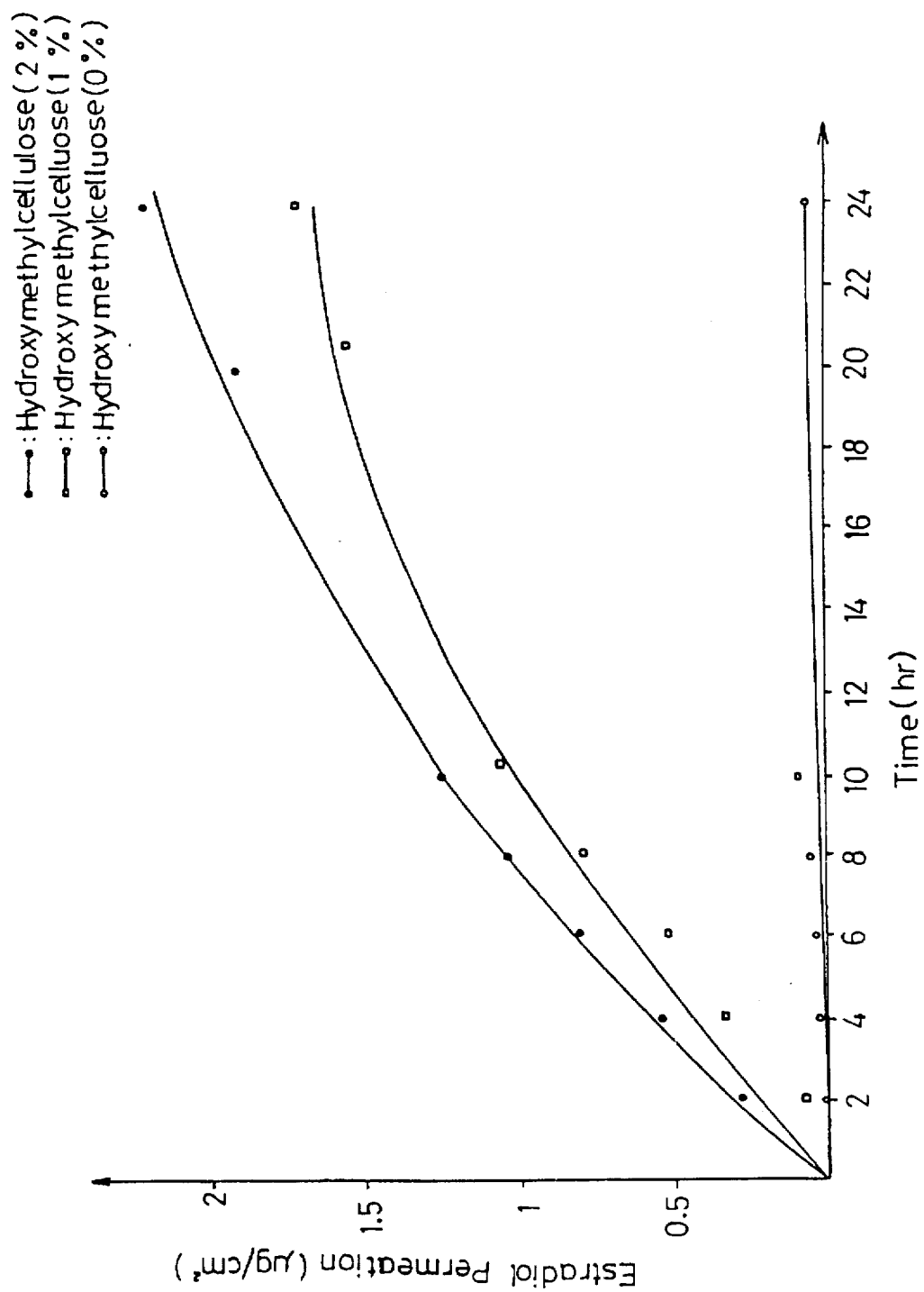
FIG. 2 is a graph showing estradiol permeation across a polymer membrane according to the present invention with time.

FIG. 2 and Table I show the estradiol permeation across the membrane in this invention. The estradiol permeation increases with increasing hydroxypropyl methyl cellulose content in the membrane. The minimal permeation of estradiol was observed in the case of membrane of COMPARATIVE EXAMPLE 1. Accordingly, the polymer membrane of the present invention is very useful for the transdermal delivery of hormones and drugs having a high solubility in ethanol and skin.

What is claimed is:

1. A process for preparing alkanol permeation polymer membrane comprising the steps of:

dissolving biocompatible, non-allergenic polymer selected from the group consisting of ethylene/vinylacetate copolymer, ethylene/vinylalchol copolymer, ethylene/ethylacrylate copolymer, vinylchloride/vinylacetate copolymer, polymethacrylate, vinylidenechloride and ethylene/vinyloxyethanol copolymer capable of being dissolved in polar organic solvent in methylene chloride to prepare a first solution;

dissolving cellulose or glycol type polyol compounds selected from the group consisting of hydroxypropylcellulose, hydroxypropylmethylcellulose, polyethyleneglycol, glycerin and ethyleneglycol in cosolvent composed of alkanol and methylene chloride to prepare a second solution;

mixing said first solution with said second solution; and casting said mixed solution on a glass plate with a controlled thickness;

evaporating the solvent and cosolvent to obtain a polymer membrane.

2. The process of claim 1, wherein the added amount of said cellulose or glycol type polyol compound is 1 to 30 wt % with respect to said biocompatible, non-allergenic polymer capable of being dissolved in polar organic solvent.

3. The process of claim 1, wherein said alkanol of cosolvent for cellulose or glycol type polyol compound is selected from the group consisting of $C_2$ to $C_8$ alkanols including ethanol, propanol, butanol, pentanol, hexanol, heptanol and octanol.

4. An alkanol permeation polymer membrane prepared by the process comprising the steps of:

dissolving biocompatible, non-allergenic polymer selected from the group consisting of ethylene/vinylacetate copolymer, ethylene/vinylalchol copolymer, ethylene/ethylacrylate copolymer, vinylchloride/vinylacetate copolymer, polymethacrylate, vinylidenechloride and ethylene/vinyloxyethanol copolymer capable of being dissolved in polar organic solvent in methylene chloride to prepare a first solution;

dissolving cellulose or glycol type polyol compounds selected from the group consisting of hydroxypropylcellulose, hydroxypropylmethylcellulose, polyethyleneglycol, glycerin and ethyleneglycol in cosolvent composed of alkanol and methylene chloride to prepare a second solution;

mixing said first solution with said second solution; and casting said mixed solution on a glass plate with a controlled thickness;

evaporating the solvent and cosolvent to obtain a polymer membrane.

* * * * *